(12) United States Patent  
Lovshin

(10) Patent No.: US 9,102,993 B1  
(45) Date of Patent: Aug. 11, 2015

(54) MINERAL PROCESSING

(71) Applicant: Albert Lovshin, Butte, MT (US)

(72) Inventor: Albert Lovshin, Butte, MT (US)

( * ) Notice: Subject to any disclaimer, the term of this patent is extended or adjusted under 35 U.S.C. 154(b) by 7 days.

(21) Appl. No.: 13/786,236

(22) Filed: Mar. 5, 2013

Related U.S. Application Data

(63) Continuation-in-part of application No. 12/819,152, filed on Jun. 18, 2010, now Pat. No. 8,410,397.

(51) Int. Cl.
| | |
|---|---|
| *B23K 26/00* | (2014.01) |
| *C22B 1/00* | (2006.01) |
| *C22B 4/04* | (2006.01) |
| *G01N 25/00* | (2006.01) |
| *B03B 13/04* | (2006.01) |
| *B65G 65/23* | (2006.01) |

(52) U.S. Cl.
CPC ... *C22B 1/00* (2013.01); *C22B 4/04* (2013.01); *G01N 25/005* (2013.01); *B03B 13/04* (2013.01); *B65G 65/23* (2013.01)

(58) Field of Classification Search
CPC ...... G01N 25/005; B65G 65/23; B03B 13/04; B07C 5/344; B07C 5/3425
USPC ............ 219/121.85, 121.6, 121.61, 576, 552, 219/586; 209/11, 127.2, 182
See application file for complete search history.

(56) References Cited

U.S. PATENT DOCUMENTS

| | | | |
|---|---|---|---|
| 7,541,557 B2 * | 6/2009 | Voloshyn et al. | ............. 209/576 |
| 2006/0175232 A1 * | 8/2006 | Voloshyn et al. | ............. 209/577 |

* cited by examiner

*Primary Examiner* — Thinh T Nguyen  
(74) *Attorney, Agent, or Firm* — CIONCA Law Group P.C.; Marin Cionca

(57) ABSTRACT

Methods and systems for processing ores by assaying the ore to determine what ore constituent has to be separated, by controlling the volume of ore processed at one time, and/or by controlling the amount of heat added to or extracted from the ore.

8 Claims, 8 Drawing Sheets

MINERAL PROCESSING

CROSS-REFERENCE TO RELATED APPLICATIONS

This application is a continuation-in-part and claims the benefit of the U.S. Non-provisional application Ser. No. 12/819,152 filed Jun. 18, 2010, which claimed the benefit of U.S. Provisional Application No. 61/268,916, filed Jun. 18, 2009. Both prior filed applications mentioned above are hereby incorporated by reference to the extent that they are not conflicting with the present application.

BACKGROUND OF THE INVENTION

1. Field of the Invention

The present invention relates generally to mining technology and more particularly to environmentally safe mineral processing.

2. Description of the Related Art

Currently, minerals in ore bodies can be extracted using environmentally unsafe techniques. Such a technique is the cyanide leaching. Expensive and still risky, lined environmental pits have to be designed and constructed in order to attempt to catch and hold the toxic chemicals, and prevent them from leaking into the ground water. Monitor wells have to be drilled and continuous monitoring have to be performed by highly trained staff. Often, the liner of the environmental pits breaks and the dangerous chemicals infiltrate and compromise the ground water.

Another technique currently used to extract minerals from ores is the flotation technique. This technique is also expensive and environmentally unsafe. Furthermore, these existing mineral processing techniques require the approval of the Environmental Protection Agency (EPA), which means that, even if assuming that these techniques will be ultimately approved, which is not always the case, additional expenditures of money and time have to be incurred by an interested party. In fact, gold mines are closed down and can't open due to the fact that cyanide leaching is no longer allowed. Moreover, low grade ore bodies are too expensive to process using these techniques.

The problems and the associated solutions presented in this section could be or could have been pursued, but they are not necessarily approaches that have been previously conceived or pursued. Therefore, unless otherwise indicated, it should not be assumed that any of the approaches presented in this section qualify as prior art merely by virtue of their presence in this section of the application.

BRIEF SUMMARY OF THE INVENTION

The above described problems are solved by the present invention. The present invention teaches a dry mineral processing technique using ore element's specific heat, and uses no harsh chemicals. Thus, this is an environmentally safe mineral processing technique. Therefore, no EPA approval and no environmental pit and no monitoring are required in order to practice the teachings of the present invention. Gold mines, which have been closed due to the fact that cyanide leaching is no longer allowed, may open and operate using the technique of the present invention. Other mines may be able to open as well since impurities are removed by the present invention's technique, thus allowing smelting without causing environmental air pollution. Furthermore, low grade ore bodies may be processed as this is an inexpensive mineral processing technique. Moreover, all the valuable minerals can be extracted from the ore in a single process, which considerably reduces the expenses with the ore processing and the overall mining operating costs.

BRIEF DESCRIPTION OF THE DRAWINGS

For exemplification purposes, and not for limitation purposes, embodiments of the invention are illustrated in the figures of the accompanying drawings, in which.

DETAILED DESCRIPTION OF THE INVENTION

Figure 1:
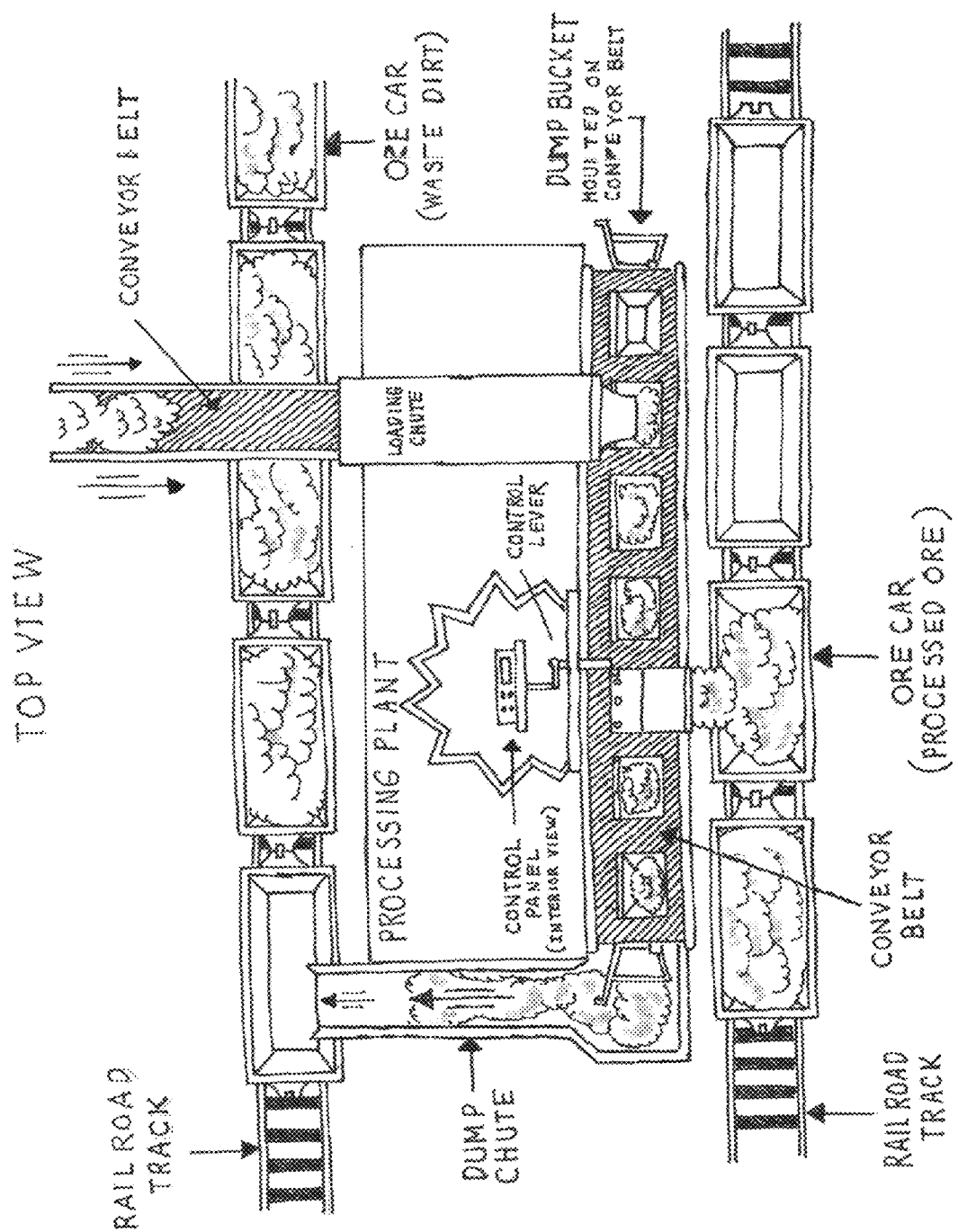
FIG. 1 illustrates the top view of a pilot plant for processing ores.

What follows is a detailed description of specific embodiments of the invention in which the invention may be practiced. Reference will be made to the attached drawings, and the information included in the drawings is part of this detailed description. The specific embodiments of the invention, which will be described herein, are presented for exemplification purposes, and not for limitation purposes. It should be understood that structural and/or logical modifications could be made by someone of ordinary skills in the art without departing from the scope of the present invention. Therefore, the scope of the present invention is defined only by the accompanying claims and their equivalents.

It is to be understood that the terms dump box, dump bucket and cup are used herein interchangeably as they mean the same thing in this context.

Figure 2:
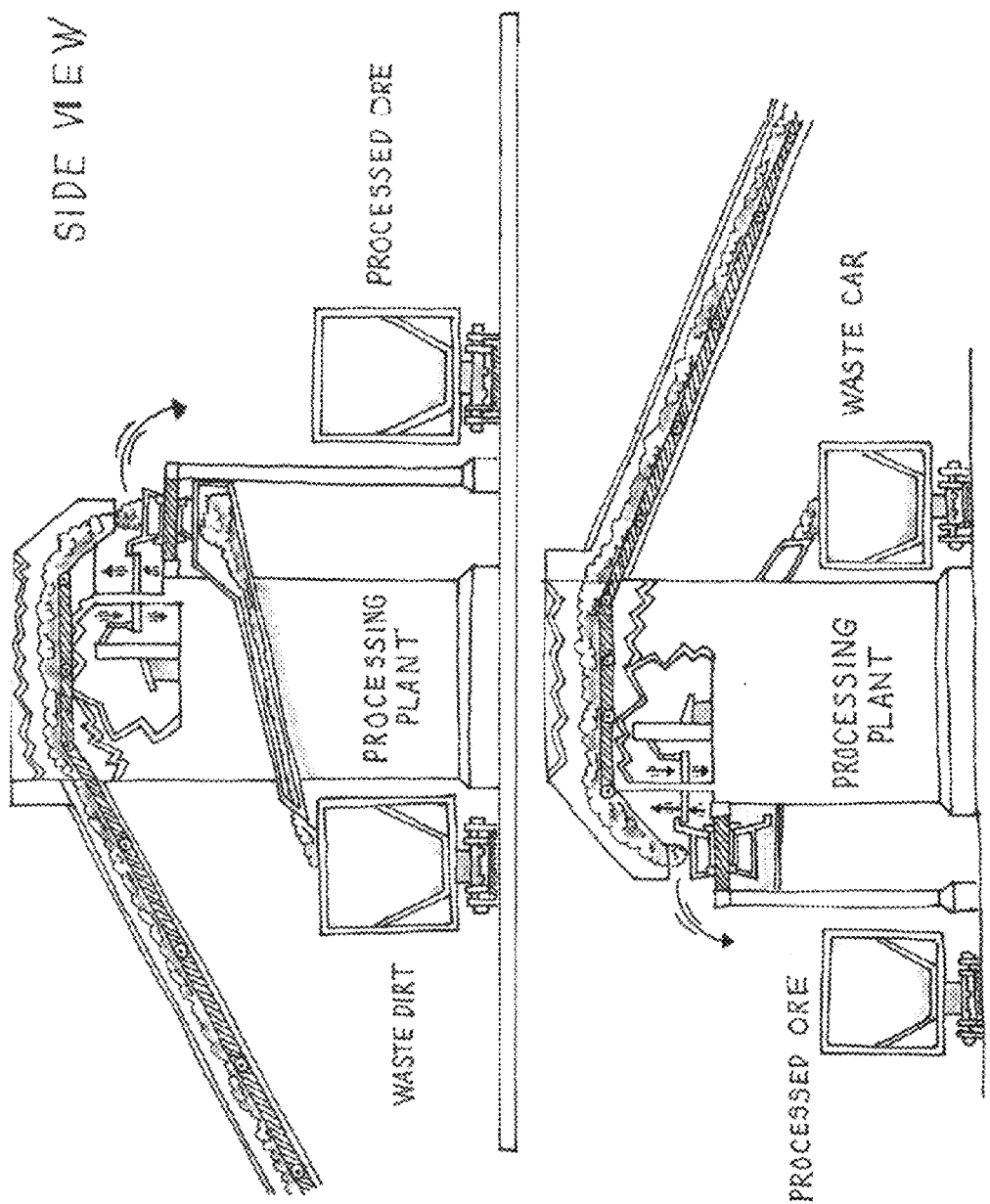
FIG. 2 illustrates the side views of the same pilot plant for processing ores.

FIG. 1 illustrates the top view of a pilot plant for processing ores. This is a diagrammatic representation of a sample plant structure that may be used to practice the present invention. FIG. 2 illustrates the side views of the same pilot plant for processing ores.

Figure 3:
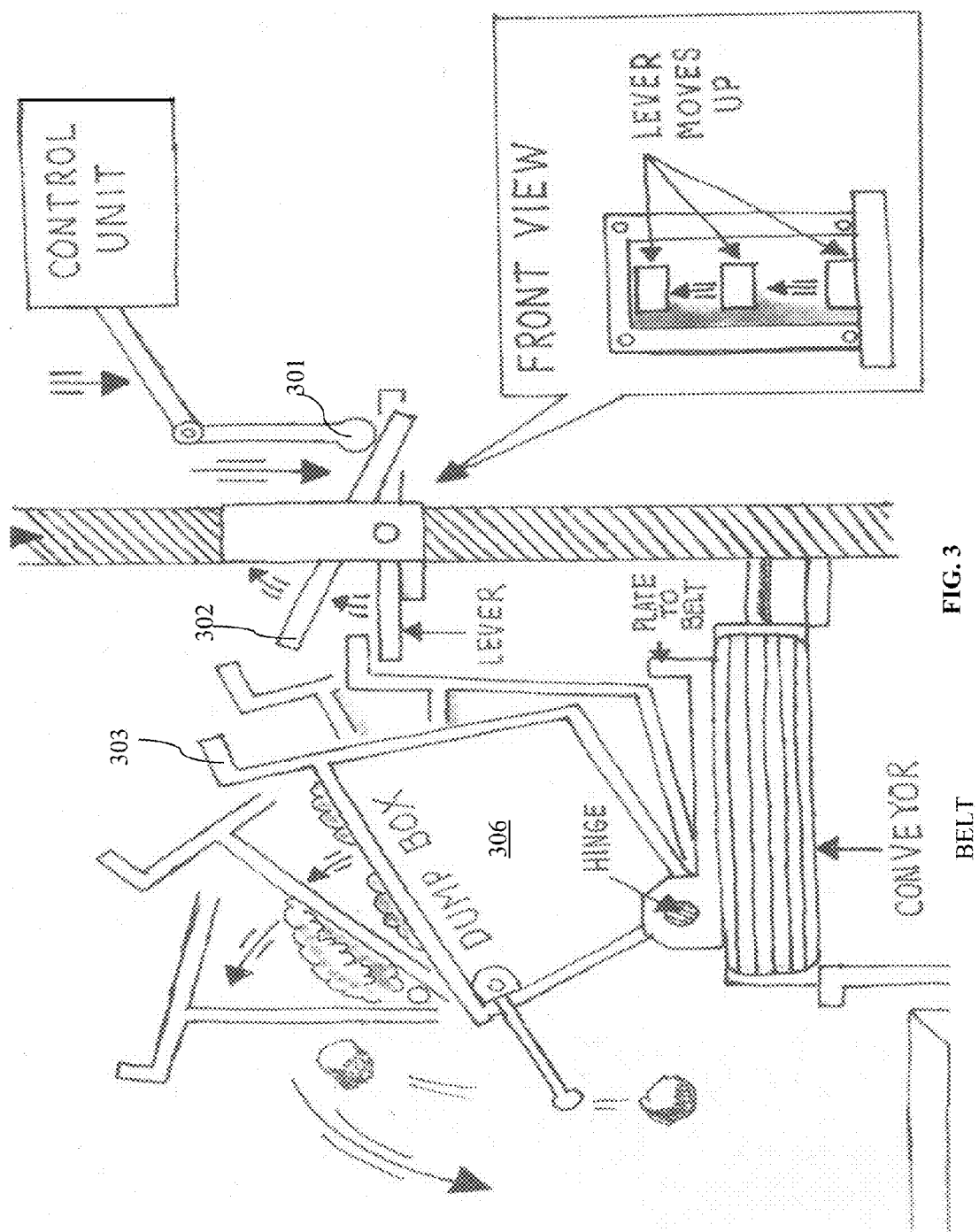
FIG. 3 shows a cup 306 being dumped over the side into a bin, using a dumping mechanism comprising a striking part 301, a lever 302 and an L-shape arm 303, in accordance with an embodiment of the present invention.

FIG. 3 shows a cup 306 being dumped over the side into a bin, using a dumping mechanism comprising a striking part 301, a lever 302 and an L-shape arm 303, in accordance with an embodiment of the present invention. The cup 306 is mounted to the conveyor belt using one hinge on one of the edges of the cup's bottom so that the cup 306 may engage in pivotal motion when its L-shape arm is struck by a lever 302, which in turn is struck by a computer-controlled striking part 301. While other dumping mechanisms are known in the art and may be used with the present invention, this particular approach may be preferred as it ensures a fast dumping, which is critically important here. This is because the one piece of ore in each cup is quite small (e.g., 1/16×1/16×1/16 inches), and therefore, a fast dumping is necessary in order to achieve a practical efficiency of the ore processing system using the teachings of the present invention. One of ordinary skills in the art would recognize that other fast dumping mechanisms and/or techniques may be used without departing from the scope of the present invention.

Figure 4:
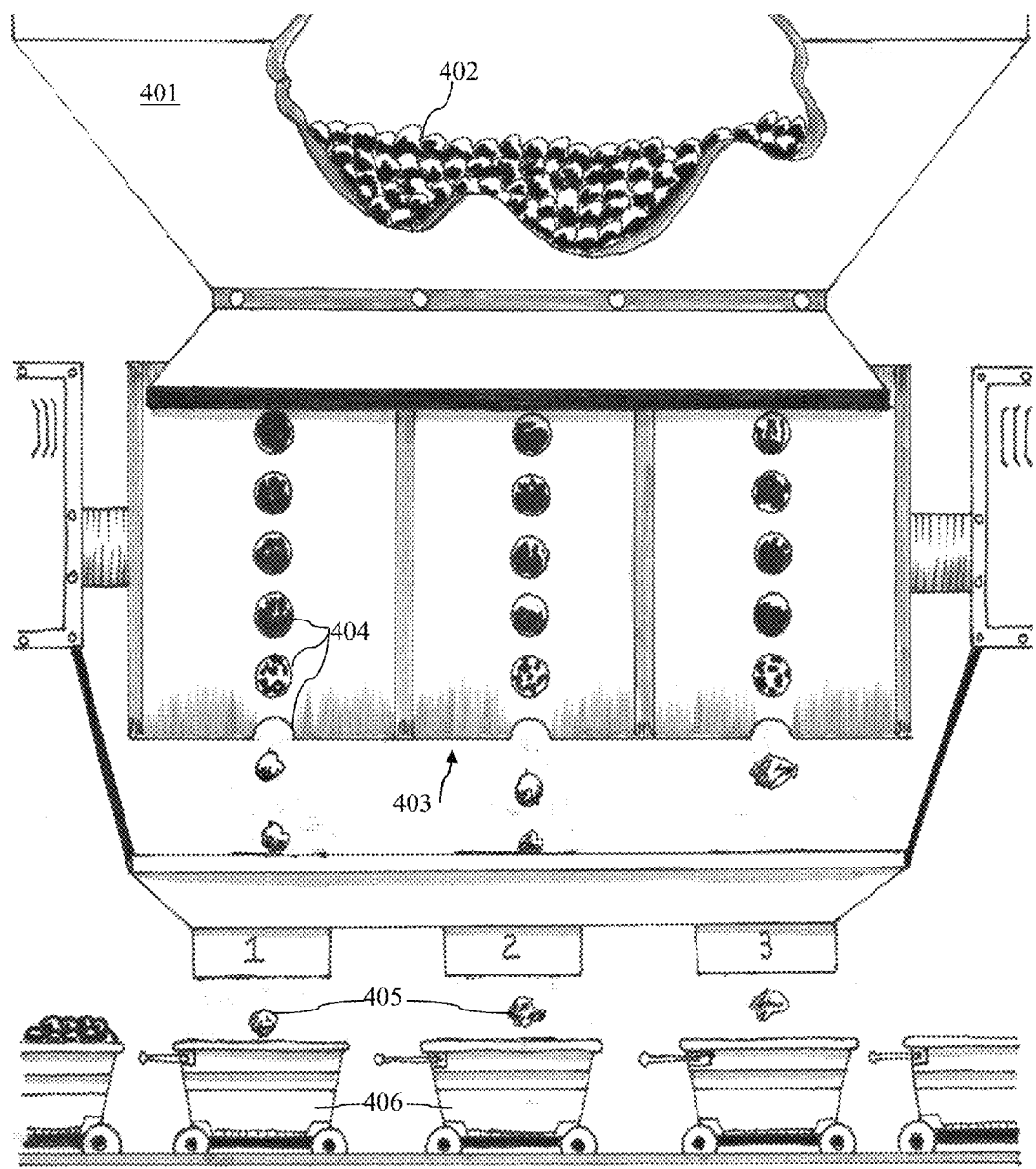
FIG. 4 illustrates the front view of a system for filling up the cup 406 with one piece of ore 405, the system comprising the feeder 401, which contains the ore 402, and, the drum 403 with its holes 404.

FIG. 4 illustrates the front view of a system for filling up the cup 406 with one piece of ore 405, the system comprising the feeder 401, which contains the crushed ore 402, and, the drum 403 with its holes 404. The ore 402 is first crushed and screened to a desired size as for example 3/16 inches (i.e., 3/16×3/16×3/16 inches) and then loaded into the feeder 401. The holes 404 in the drum 403 are made of a necessary size in order to accommodate a piece of ore of the size chosen (e.g., 3/16 inches). When turning against the ore 402, the drum's holes 404 are filled with a piece of ore. Later, when the drum's holes 404 are above the cups 406 the pieces of ore 405 are gravitationally transferred from the drum's holes 404 to the cups 406. The cups 406 are then transported by the conveyor belt to the processing area (i.e., the 3-boxes or 5-boxes area described below) and ultimately to the appropriate dumping bin.

Figure 5:
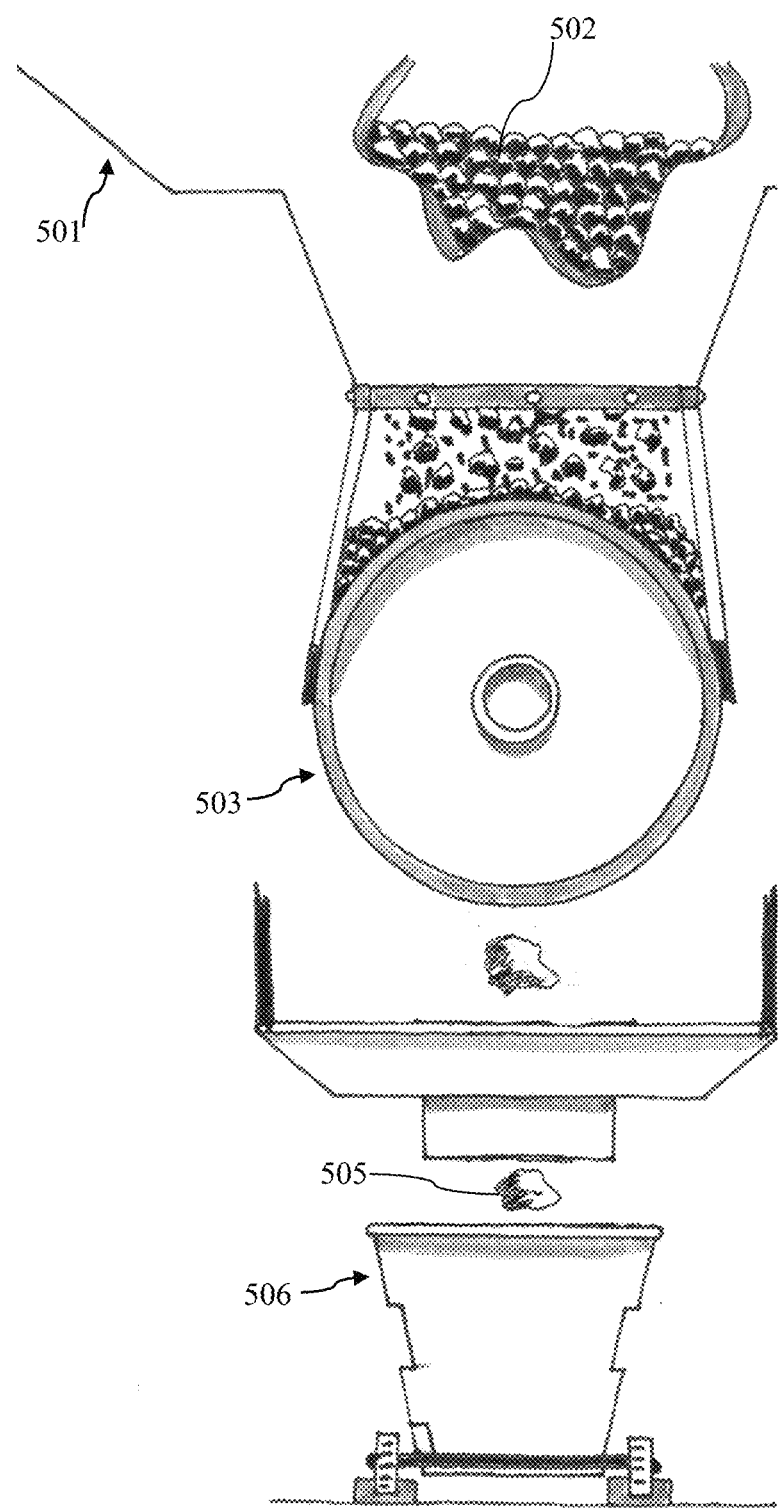
FIG. 5 illustrates the side view of the same system for filling up the cup 506 with one piece of ore 505, the system comprising the feeder 501, which contains the ore 502, and, the drum 503 with its holes (not shown).

FIG. 5 illustrates the side view of the same system for filling up the cup 506 with one piece of ore 505, the system comprising the feeder 501, which contains the crushed ore 502, and, the drum 503 with its holes (not shown).

Figure 6:
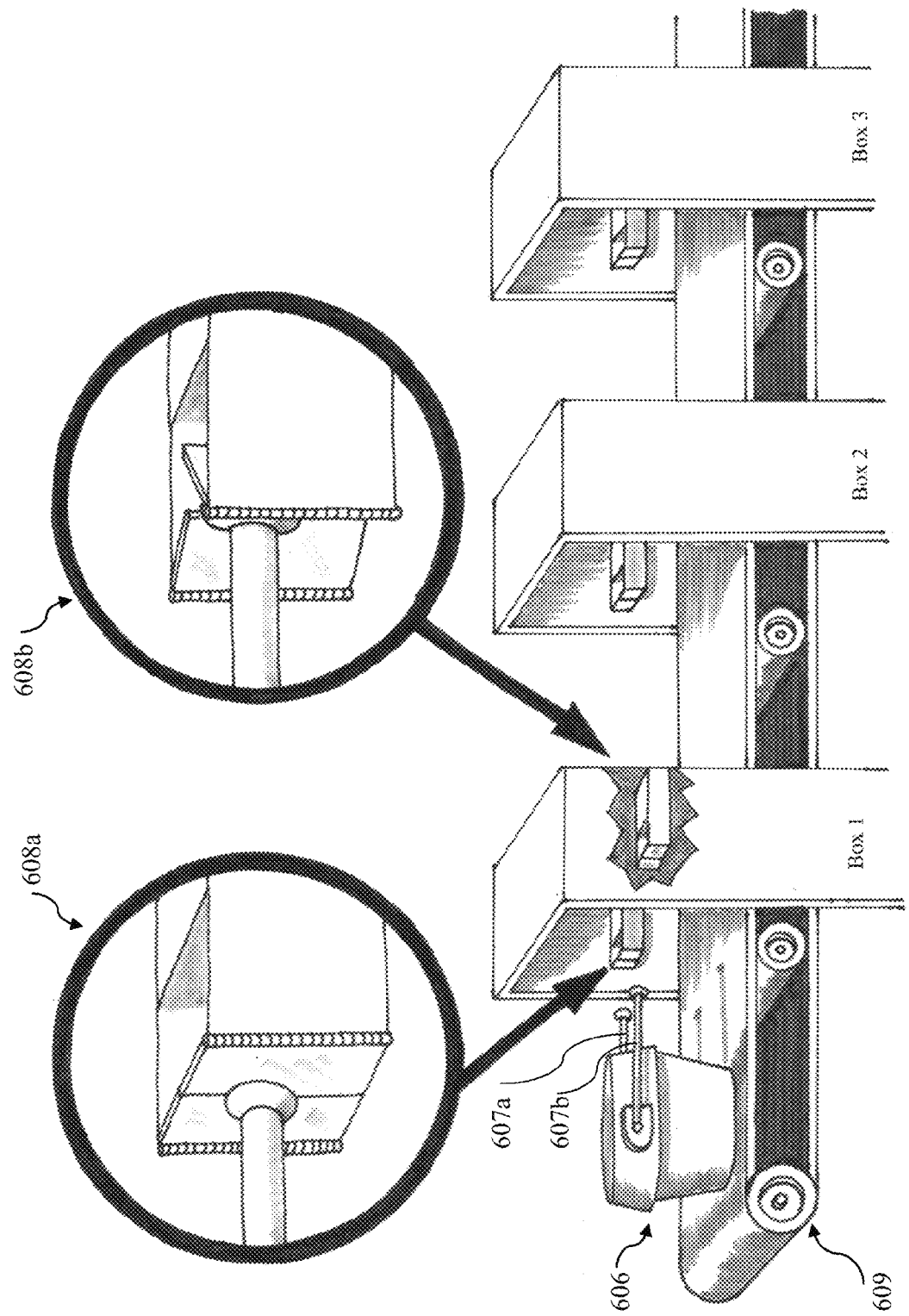
FIG. 6 illustrates the perspective view of a three-box conveyor 609 for processing the ore (not shown) from cup 606; the cup 606 has two arms 607a and 607b attached to it and designed to pass through and make contact with guides 608a and 608b respectively, in accordance with several embodiments of the present invention.

FIG. 6 illustrates the perspective view of a three-box conveyor 609 for processing the ore (not shown) from cup 606; the cup 606 has two arms 607a and 607b attached to it and designed to pass through and make contact with guides 608a and 608b respectively, in accordance with several embodiments of the present invention. FIG. 6 depicts a 3-box system for practicing a preferred method (3-box method) for processing ores based on the differences in specific heat, in accordance with the teachings of the present invention. Box 1 contains a digital optical thermometer that can take two thousand temperature measurements a second with an accuracy of 0.01 degree (one hundredth of a degree centigrade). Such a thermometer is available commercially. Box 1 also contains a means to measure temperature by contact using a digital contact thermometer. Other quick and precise temperature measurement tools may be employed without departing from the scope of the present invention. The ore cup 606 is made like a hot plate. Furthermore, each ore cup 606 has a unique bar code that can be read by a bar code scanner.

Box 2 contains a laser that can send a laser beam of power in watts to heat up the ore piece in cup 606 with exact amount of calories of heat. Box 2 may also contains a direct current supply that can heat the cup with a precise amount of calories of heat. Other quick and precise heating (or cooling) tools and/or equipment may be employed without departing from the scope of the present invention. Box 1, 2 and 3, also contains a bar code reader.

When the ore cup 606 enters box 1, the digital optical thermometer determines the temperature of the piece of ore in the ore cup 606. The bar code of ore cup 606 is determined by the barcode reader. The temperature of the piece of ore in the cup may be also determined by the contact thermometer. The arms 607a and 607b of the cup 606 make contact with the metal guides 608a and 608b, hence, allowing contact temperature measurement to be made. The ore cup's 606 bar code, the digital optical temperature of the ore in the ore cup 606, the contact temperature of the piece of ore in the ore cup 606 is sent to the computer.

Next, the ore cup 606 enters box 2 where the laser sends a laser pulse of a precise calorie of heat to heat the piece of ore in the ore cup 606. If the laser is not used, the arms 607a and 607b make contact with the metal guides 608a and 608b and a precise amount of power is added to the piece of ore in the cup 606 by the direct current supply. The current supply sends a precise amount of power to the hot plate cup 606 to add the precise amount of calories of heat to the piece of ore.

Next, the ore cup 606 enters box 3. Box 3 is the same as box 1. The digital optical thermometer determines the temperature of the piece of ore in the ore cup 606. The contact thermometer may also determine the temperature of piece of ore in the ore cup 606. The temperature of the piece of ore from the digital optical thermometer and/or the digital contact thermometer is sent to the computer. The bar code of the ore cup is sent to the computer.

It is well known that the heat (in calories (cal)) gained or lost by a body in which there is no change of state equals mass (in grams (g)) times specific heat (in cal/gc) times temperature change (in centigrade (c)).

The computer has the initial temperature of the piece of ore and the temperature after the precise amount of heat is added. The computer subtracts the initial temperature from the second temperature; this is the temperature change. In this ore body example (see below), we have nine minerals in pieces of approximately 0.004 cubic centimeters. Each piece can vary by plus or minus ten percent in one percent increments. This results in 189 (21×9) different mineral piece size possibilities. The computer has the specific heat of all the nine items. The computer has already calculated the temperature change of the 189 different items. The computer has already selected the calories of heat (e.g., 0.1 cal-0.5 cal) to add the ore samples by considering factors such as the size of the mineral piece, the specific heat and the flash point of the respective mineral (i.e., coal in this example). This is important, as, for example, too much heat may burst the mineral piece into flame.

The computer has already calculated 189 possible temperature changes. A range (e.g., +/−3%) of the temperature changes may also be calculated and used by the computer considering factors such as the variation in the sizes of the ore pieces being processed. Therefore, the computer has a look up table that contains all the possible temperature changes, the mass, the specific heat, the name of the mineral, the density and the calorie of heat used. Hence, the computer uses the look up table to determine what the mineral is (e.g., coal, platinum, etc) based on the temperature change, and/or the respective ranges, previously calculated for each mineral. If the temperature change calculated by subtracting the temperature measured in box 1 from the temperature measured in box 3, equals or falls into the range of the expected temperature change of a certain mineral, previously calculated and tabulated by the computer, then the computer "knows" what the mineral is.

The bar code of the ore cups are sent to the computer. The computer activates the dump mechanism when the ore cup 606 is at the correct ore car containing the mineral in the ore cup. Each ore car has bar code reader; as the ore cups bar pass over the bar code reader, the computer knows the contents of the ore cup 606 and activates the dump mechanism when the ore cup passes over the correct ore car.

An alternative way of using this processing method is to "tell" the computer in advance what ore is actually being processed. For example, if coal ore is being processed, the computer would be instructed that coal should be expected in the cup 606. So, after calculating the temperature change, the computer would use the look up table only to verify that, indeed, coal is in the cup 606 and dump it in the coal car. If not coal, the piece of ore in cup 606 would be dumped in a different car (e.g., a waste or special car).

The only way that two different samples may have the same temperature is if the mass of one of the samples is numerically equal to the specific heat of the other sample. In this ore body example (see above) we have nine different elements, thus, nine different specific coefficients of heat. N things taken P at a time equals N-factorial divided by P-factorial times (N–P) factorial; in this example N=9 and P=2; 9 factorial=362880 and 7 factorial=5040. Combinations=362880/(5040×2)=36. The computer calculates these possibilities, where two elements can have the same temperature change, in advance, and dumps those ore pieces into special bins.

When determining the proper size for the ore to be crushed at, several factors may have to be considered. It is to be noted that the smaller the ore piece, the more obvious the temperature change difference, due to the presence of impurity, appears to be. This means that it may be easier for the computer to detect the ore pieces which have impurities and dump them to the appropriate bins or cars. Therefore, a more precise separation of the pure ore from the impure ore may be achieved. Thus, greater reliability of the processing technique and system exists. The power of the heating source available (e.g., laser) may need to be considered as well. The larger the ore piece, the more powerful the heating source have to be.

If the ore piece is too small for a particular power of the heating source, the ore piece could burst into flames. Obviously, the greater the ore piece, the more efficient the processing system is as more ore may be processed in the same amount of time. A balancing act has to be performed here to achieve the right equilibrium between reliability and efficiency of the processing system. For example, for coal, the 1/16 inch size (i.e., 1/16 by 1/16 by 1/16) appears to be the right size of the ore piece for a laser currently available on the market.

To process a large amount of ore, conveyor belts with, for example, 4,000 ore cups 606 and three boxes (i.e., Box 1 plus Box 2 plus Box 3). Each box of three may be able to process two thousand ore cups a second. Using copper as an example, each ore cup contains 7 grams of ore; 7 times 2,000 times equals 14,000 grams a second. This equals 30.83 pounds a second, 1850.22 pounds a minute, or 55.5 tons an hour. This is one dump truck an hour. So, if you have 80 dump trucks, you may need to have 80 conveyor belts.

Figure 7:
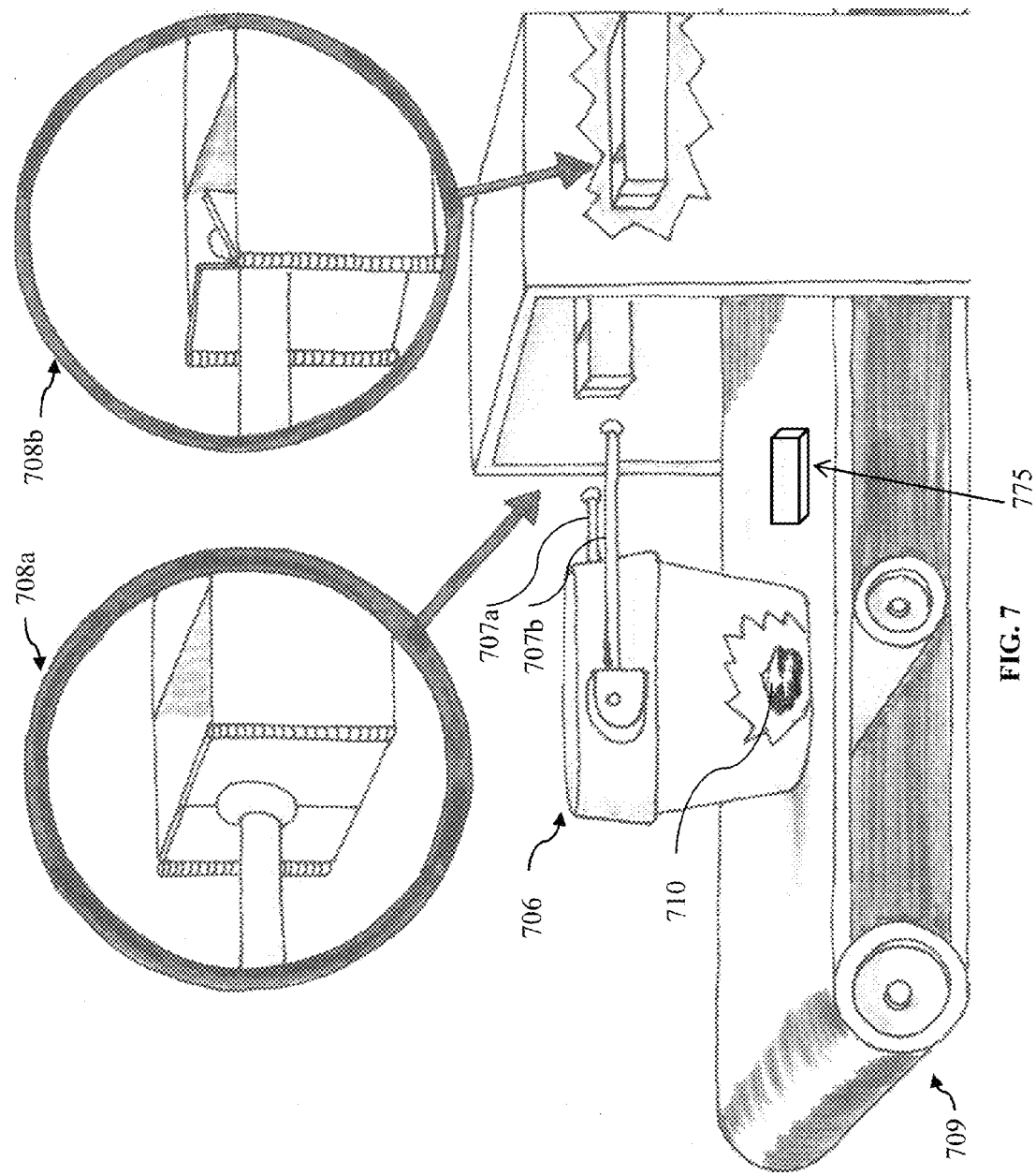
FIG. 7 illustrates the partial perspective view of a conveyor 709 for processing the ore 710 from cup 706; the cup 706 has two arms 707a and 707b attached to it and designed to pass through and make contact with guides 708a and 708b respectively, in accordance with several embodiments of the present invention.

FIG. 7 illustrates the partial perspective view of a conveyor 709 for processing the ore 710 from cup 706; the cup 706 has two arms 707a and 707b attached to it and designed to pass through and make contact with guides 708a and 708b respectively, in accordance with several embodiments of the present invention.

Figure 8:
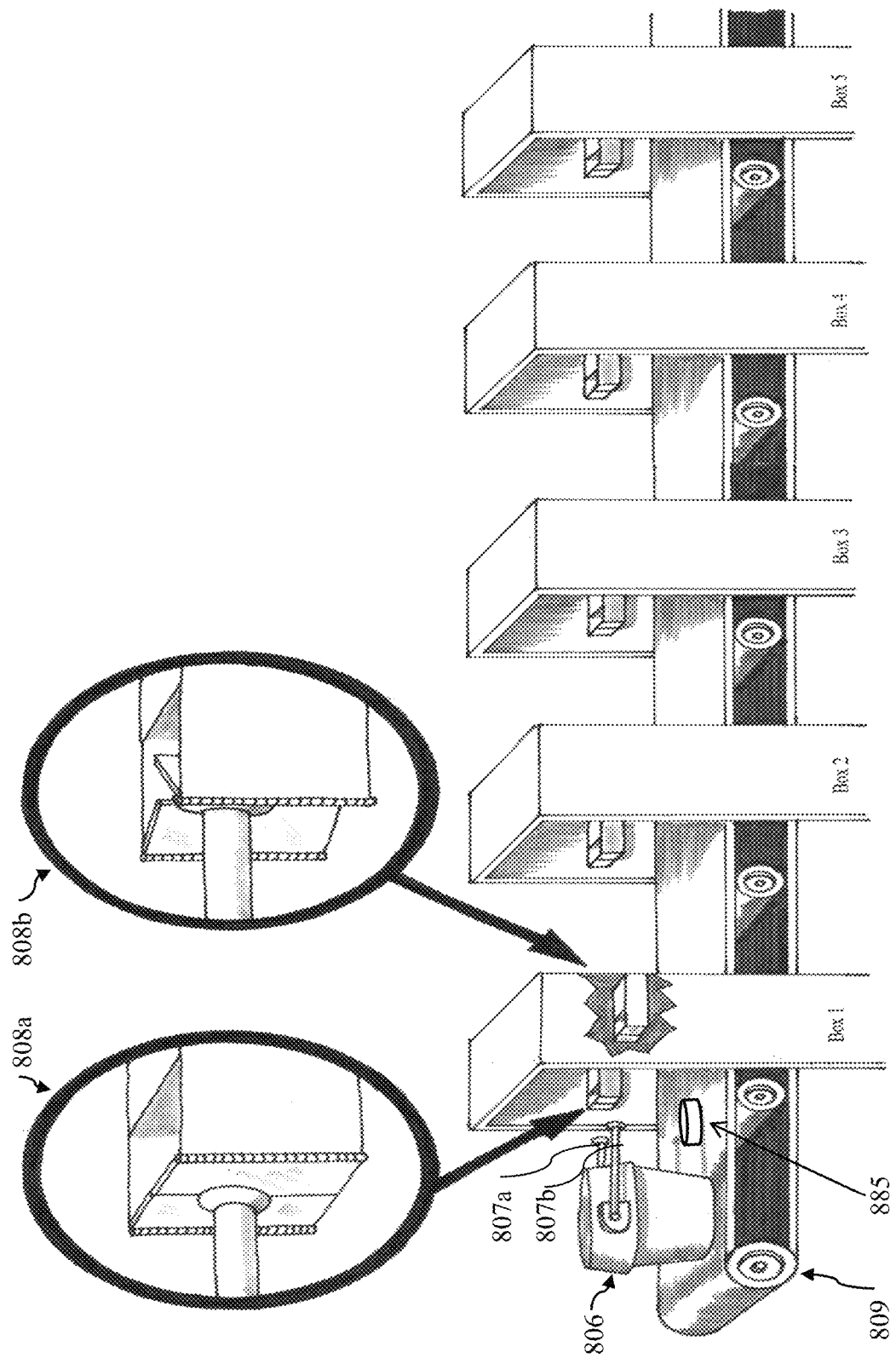
FIG. 8 illustrates the perspective view of a five-box conveyor 809 for processing the ore (not shown) from cup 806; the cup 806 has two arms 807a and 807b attached to it and designed to pass through and make contact with guides 808a and 808b respectively, in accordance with several embodiments of the present invention.

FIG. 8 illustrates the perspective view of a five-box conveyor 809 for processing the ore (not shown) from cup 806; the cup 806 has two arms 807a and 807b attached to it and designed to pass through and make contact with guides 808a and 808b respectively, in accordance with several embodiments of the present invention. FIG. 8 depicts a 5-box system for practicing another preferred method (5-box method) for processing ores based on the differences in specific heat, in accordance with the teachings of the present invention. The advantage of this method is that, after crushing and screening the ore body to, for example, 1/16 inch pieces (i.e., 1/16 inches by 1/16 inches by 1/16 inches), variation in the size of the ore pieces does not impair the accuracy of the ore processing based on differences in minerals' specific heat.

Boxes 1, 2 and 3 in FIG. 8 are identical as the boxes 1, 2 and 3 in FIG. 6, respectively. Furthermore, box 4 is identical with box 2 and box 5 is identical with box 3.

For exemplification purposes, let's assume that the ore being processed is coal. The ore body is crushed and screened to a desired size, as for example, 1/16 inch (i.e., 1/16 inches by 1/16 inches by 1/16 inches). Again, it is not important if the pieces of ore vary in size, as for example, with +/−3%. Next the pieces of ore (i.e., coal in this example) are loaded into the cups as described earlier (see FIGS. 4 and 5). Therefore, the cup 806 contains a piece of coal. In box 1, one or both of the thermometers described above measure the temperature of the piece of ore (i.e., coal in this example) in the cup 806 and the bar code reader reads the bar code of the cup 806. The temperature of the piece coal and the bar code of the cup 806 are sent to the computer. The computer determines the exact quantity of heat to use for heating the mineral piece by considering factors such as the size of the mineral piece, the specific heat and the flash point of the respective mineral (i.e., coal in this example). This is important, as, for example, too much heat may burst the mineral piece into flame.

Next the cup 806 enters box 2, where a laser beam of computer-predetermined quantity of heat (e.g., 0.1 (i.e., 1/10) calorie) is sent to the piece of coal in the cup. As, described earlier, a direct current of known power can also heat the piece of coal.

Next, in box 3, the temperature of the piece of coal is measured again and sent to the computer. The computer determines the first temperature change by subtracting the temperature measured in box 1 from the temperature measured in box 3. Using the specific heat for coal, the density of the coal, the amount of heat used and the just-calculated first temperature change, the computer calculates the mass of the coal piece in cup 806. The formula used by the computer is: Heat added=(specific heat)(mass)(temperature change), or, Mass=(heat added)/((specific heat)(temperature change)). Since coal is used in this example, the computer uses the specific heat of coal, which is 0.17. One of ordinary skills in the art would recognize that the mass of the coal piece in cup 806 may be calculated in different ways without departing from the scope of the present invention. For example, the weight of the ore cup 806 may be predetermined and subtracted by the computer from the weight of the ore cup 806 with the coal piece in it. Both weights may be measured using, for example, any readily available electronic weighing machine, which may be installed on the conveyor belt. The weight measurements will be sent to the computer.

The computer calculates the temperature change of this calculated mass of coal, which the computer determined earlier, using 0.5 calories of heat. Here are the underlying equations: 0.5=(mass computer calculated)(0.17×temperature change); (0.5)/((mass computer calculated)(0.17))=temperature change. Now, if the temperature change that computer calculates equals five times the temperature change obtained by subtracting the temperature measured in box 3 from the temperature measured in box 5 (i.e., the second temperature change), the piece of coal in cup 806 is pure coal.

The computer also multiplies this first temperature change by five.

Next, when the cup 806 is in box 4, the piece of coal is heat (by laser or contact) five times as much as in box 2 (e.g., 0.5 (i.e., 5/10) calorie). When the computer determines that in box 2 a certain amount of heat should be used as described earlier, the computer does so by also verifying that the five-time greater amount of heat in box 4 would not create problems such as igniting the ore piece (i.e., coal in this example). In box 5, the temperature of the piece of ore is measured again and sent to the computer. A second temperature change is calculated by the computer by subtracting the temperature measured in box 3 from the temperature measured in box 5. If this second temperature change equals five times the first temperature change calculated previously, and/or the expected temperature change based on the mass of the coal piece previously calculated, then the piece of ore in the cup 806 is pure coal and, therefore, using the bar code, the computer will activate the dumping mechanism when the cup 806 is above the car containing coal. Otherwise, the computer will ensure that the piece of ore in cup 806 is dumped in a different car (e.g., a special or waste car).

The computer can be "told" (i.e., preset and/or pre-programmed) in advance what ore is being processed (e.g., coal ore), and therefore, what mineral to expect in cup 806. Or, the computer can use the first temperature change value and the look up table to determine what the mineral is or is likely to be. Then, if the second temperature change equals five times the first temperature change, that would be the confirmation that the mineral in cup 806 is pure.

The 3-box method and the 5-box method may be employed independently of each other or in combination. A user may choose to use the 3-box method or the 5-box method. A user may also combine the two methods by, for example, using the 5-box method as a second layer of verification to increase the overall accuracy of the ore processing system. So, for example, after the temperature is measured in box 3, the computer calculates the first temperature change and looks in the existing tables to determine what the piece of ore consists of (e.g., coal).

Later, after the temperature in box 5 is measured, the computer performs a second determination by calculating the second temperature change and comparing it with the first temperature change. If the second temperature change is greater than the first temperature change by the same number of times as the number of times (e.g., five) the amount of heat in box 4 was increased (when compared with the amount of heat in box 2), that is a confirmation that the piece of ore is pure (e.g., pure coal). Boxes 4 and 5 may need to be added only if the crushed ore varies significantly in size.

Here is the mathematical reasoning behind the method described above and used by the computer:

Heat gained=(specific heat of coal)(mass of coal)(temperature change)

.1 cal.=(mass of coal)(specific heat of coal)(first temperature change)

.5 cal.=(mass of coal)(specific heat of coal)(second temperature change)

(0.1)/((mass of coal)(specific heat of coal))=first temperature change     (eq. 1)

(0.5)/((mass of coal)(specific heat of coal))=second temperature change     (eq. 2)

Multiply eq. 1 by 5

(0.5)((mass of coal)(specific heat of coal))=5(first temperature change)     (eq. 3)

Subtract equation 2 from equation equation 3

0=5(first temperature change)−(second temperature change), or,

Second temperature change=5(first temperature change)

It should be understood that similar equations apply to minerals others than coal.

It should be also understood that if the coal piece in cup 806 is pure, its temperature change is different than that of a piece of coal that contains impurities such as, for example, one percent of iron sulfide (FeS). This is because the specific heat of the impurity (e.g., FeS) is different than that of coal. Furthermore, because of the relative small quantity of the impurity (e.g., 1-3%), increasing the amount of heat added (e.g., five times) may accentuate the temperature change differences, between a piece of pure coal and a piece of impure coal, thus, making it easier for the computer to detect the impurity. Hence, the differences in temperature changes are used by the computer to determine if the piece of coal in cup 806 is pure or not, and therefore, dump it in the appropriate ore car.

Again, the specific heat of a substance is numerically equal to the number of calories required to raise the temperature of one gram of the material with one degree centigrade. The specific heat is measured in calories/gram·centigrade.

Heat (in calories) equals mass of material (in grams) times specific heat of the material (in calories/gram·centigrade) times the material's change in temperature ($Q=mc\Delta T$).

The above is a law of physics.

In the ore example used, the ore body contains the following elements with the following physical properties (according to existing literature):

| Element Name | specific heat cal/gc | density g/cc |
|---|---|---|
| Arsenic | .078 | 5.73 |
| Antimony | .0504 | 6.091 |
| Copper | .0821 | 8.9 |
| Gold | .0316 | 19.2 |
| Molybdenum | .065 | 9.01 |
| Silver | .0558 | 10.43 |
| Titanium | .0275 | 4.5 |
| Platinum | .0234 | 21.37 |
| Coal | .17 | 2.25 |

Different sizes (e.g., 1/16 inches, 3/8 inches, etc) of the sample ore may need to be tested for specific heat determination purposes. This is because it is important to determine at the outset whether or not the specific heat of the specific ore tested varies with the size of the ore piece to be processed. This could happen because, for example, heat may be reflected differently for ore pieces of various dimensions. As it is often the case in the industry, the tests may start by crushing the ore to samples of 3/8 inch by 3/8 inch by 3/8 inch; 3/8 inches=0.9525 centimeters. This has a volume of 0.864 cubic centimeters.

Next, you determine the specific heat, in one degree temperature increments, from, for example, minus 30 Fahrenheit to plus 90 Fahrenheit. The temperature range to use for testing can vary. To help in choosing the temperature range, the average temperatures in the area where the ore processing will occur may be considered. Testing the ore sample for the actual specific heat values at different temperatures is important because it is known that the specific heat of a certain material do vary depending on the actual temperature of that material. Therefore, it is important for the computer to have all this data when controlling the ore processing based on specific heat differences.

After determining the specific heat of the minerals in the sample ore, an assay may also need to be performed for the purpose of determining what the concentration (e.g., 2%) of each mineral in the ore is. This helps calculate what the expected quantities for each mineral are at the end of the processing and, by comparing the expected quantities with the actual quantities obtained, the efficiency of the processing technique may be evaluated. This information (i.e., the assay's results), the temperature, specific heat and the density of each mineral in the sample ore is then entered into a computer.

Next, the ore is crushed to 5/16 in by 5/16 in by 5/16 in; 5/16 inch=0.7937 centimeters. This has volume of 0.5 cubic centimeters. The specific heat is determined, in one degree temperature increments, from minus 30 to plus 90 F. After determining the coefficient of heat, an assay on the sample is done and this information is stored in a computer: temperature, coefficient of heat, density, and assay results.

Next, the ore is crushed to 4/16 in by 4/16 in by 4/16 in; 4/16 inch=0.635 centimeters. This has volume of 0.0156 cubic centimeters. The specific heat is determined, in one degree increments, from minus 30 to plus 90 F. After determining the coefficient of heat, an assay on the sample is done and this information is stored in a computer: temperature, coefficient of heat, density, and assay results.

Next, the ore is crushed to 3/16 in by 3/16 in by 3/16 in; 3/16 in=0.4762 centimeters.

This has a volume of 0.0066 cubic centimeters. The specific heat is determined, in one degree increments, from minus 30 to plus 90 F. After determining the coefficient of heat, an assay on the sample is done and this information is stored in a computer: temperature, coefficient of heat, density, and assay results.

Next, the ore is crushed to 2/16 in by 2/16 in by 2/16; 2/16 inch=0.3175 centimeters. This is a volume of 0.032 cubic centimeters. The specific heat is determined, in one degree increments, from minus 30 to plus 90 F. After determining the coefficient of heat, an assay on the sample is done and this information is stored in a computer: temperature, coefficient of heat, density, and assay results.

Next, the ore is crushed to 1/16 in by 1/16 in by 1/16 in; 1/16 inch=0.15875 centimeters. This has a volume of 0.004 cubic centimeters. The specific heat is determined, in one degree increments, from minus 30 to plus 90 F. After determining the coefficient of heat, an assay on the sample is done and this information is stored in a computer: temperature, coefficient of heat, density, and assay results.

For a volume of 0.864 cubic centimeters of the following minerals, and by adding 50 calories of heat, the following temperature changes are obtained:

| Name | temperature change in centigrade (c) |
| --- | --- |
| Arsenic | 129 c |
| Antimony | 188.5 c |
| Copper | 79.2 c |
| Gold | 26.2 c |
| Molybdenum | 98.82 c |
| Silver | 99.44 c |
| Titanium | 467.63 c |
| Platinum | 115.73 c |
| Coal | 151 c |

An ore piece of 1/16 in by 1/16 in by 1/16 in (i.e., a volume of 0.004 cubic centimeters) has the following mass:

| Name | Mass (grams) |
| --- | --- |
| Arsenic | .622 |
| Antimony | .024 |
| Copper | .035 |
| Gold | .0768 |
| Molybdenum | .036 |
| Silver | .04172 |
| Titanium | .018 |
| Platinum | .0854 |
| Coal | .009 |

Adding one tenth of a calorie of heat to the following, at a volume of 0.004 cubic centimeters, results in a temperature change of:

| Name | temperature change in centigrade |
| --- | --- |
| Arsenic | 58.2 c |
| Antimony | 82.67 c |
| Copper | 34.8 c |
| Gold | 41.25 c |
| Molybdenum | 42.6 c |
| Silver | 42.9 c |
| Titanium | 87.16 c |
| Platinum | 50.8 c |
| Coal | 65.3 c |

Adding one half of a calorie of heat to the following, at a volume of 0.004 cubic centimeters, results in a temperature change of:

| Arsenic | 291 c |
| --- | --- |
| Antimony | 413 c |
| Copper | 174 c |
| Gold | 206.02 c |
| Molybdenum | 213.43 c |
| Silver | 214.77 c |
| Titanium | 435.8 c |
| Platinum | 254 c |
| Coal | 326 c |

It is to be noted that, as expected, when a higher amount of heat is added, the temperature changes are greater, hence, easier for the computer to differentiate between the different minerals and/or pure/impure minerals. However, as noted earlier, when selecting the right amount of heat to be added, other factors have to be considered such as the flash point of the particular ore being processed and the size of the ore piece.

After the specific heat is determined for all the different densities, the computer calculates, for a known value of calorie of heat added to the samples, the temperature change from one percent increase in volume to an increase of ten percent in volume for each unique specific heat. For example, starting with volume 0.004 cubic centimeters and then, 0.00404, 0.00408, 0.00412, 0.00416, 0.0042, 0.00424, 0.00428, 0.00432, 0.00436, 0.0044 (all in cubic centimeters). And then, the computer calculates the temperature change for each unique specific heat for decrease in volume from one percent to ten percent in increments of one percent. For example, 0.004, 00396, 0.00392, 0.00388, 0.00384, 0.0038, 0.00376, 0.00376, 0.00372, 0.00368, 0.00364 (all cubic centimeters).

This testing may be necessary as the ore pieces in the crushed ore may vary in size. It is common in the industry to have a +/−3% variation in ore piece size. A greater variation (e.g., +/−10%) may be chosen, just to be on the safe side. All this data comprising the various temperature changes for various ore piece sizes may need to be loaded into the computer. Therefore, the computer would have a range of temperature changes associated with a particular mineral. When the computer will detect a temperature change falling within the prescribed range of temperature changes associated with a particular mineral the computer will "know" what the mineral is and it will dump it in the appropriate bin.

If this isn't accurate enough the increments become 0.001 increments (tenth of a percent). All of the above information is stored in a computer look up table.

The computer has all densities of the ore crushed at various different volumes. The computer has the specific heat of all of the different components of the ore body. The computer calculates the temperature change of the various ore components at a known volume starting 0.004 cubic centimeters starting with 0.01 calories of heat for all of the different specific heat at 0.004 cubic centimeters. The computer, in increments of 0.01 calories up to one calorie, calculates the temperature change of the various different specific heats at volume 0.004 cubic centimeters.

The computer does the same for the volume 0.004 cubic centimeters from one percent increase in volume: 0.00404 cc, 0.004008 cc, 0.004012 cc, 0.004016 cc, 0.004020 cc, 0.004024, 0.004028, 0.004032 cc, 0.004036 cc, 0.00404 cc.

The computer does the same for 0.004 cubic centimeters from one percent decrease in volume to a ten percent decrease in volume in one percent increments: 00396 cc, 0.00392 cc, 0.00388 cc, 0.00384 cc, 0.00380 cc, 0.00376 cc, 0.00372 cc, 0.00368 cc, 0.00364 cc, 0.00360 cc.

For the ore body in this example the computer has a total of 2100 possible different temperatures for 0.004 cubic centimeters with an increase of ten percent in volume to a decrease in volume of ten percent.

The computer picks the calorie of heat that you need to add to the 0.004 cubic centimeters to be able to tell exactly what the sample is exactly out of the one hundred eighty one (181) different possibilities various mineral volume variations at 0.004 cubic centimeters with a plus or minus 10 percent volume variation.

Whatever volume it is decided to crush the ore to, the computer determines the exact calorie of heat to use (e.g., 0.1 cal, 0.3 cal, 0.5 cal, etc) in order to make the temperature changes the most distinguishable possible and to be able to determine exactly the ore elements to be separated.

For the sample ore used here, the following data may need to be preloaded into the computer:

For Arsenic:

| Volume (cc) | mass (g) |
|---|---|
| .004 | .02292 |
| .00396 | .02269 |
| .00392 | .0224616 |
| .00388 | .0222324 |
| .00384 | .0220032 |
| .00380 | .021774 |
| .00376 | .0215448 |
| .00372 | .02213256 |
| .00368 | .0210864 |
| .00364 | .0208572 |
| .00360 | .020628 |

The corresponding temperature changes in centigrade (c), at one calorie of heat: 559.75, 565.83, 570.77, 576.65, 583.66, 588.79, 595.06, 601.46, 607.99, 614.68, 621.50.

For Copper, one calorie of heat:

| Volume (cc) | mass (g) | temperature change (c) |
|---|---|---|
| .0044 | .03916 | 311.03 |
| .00436 | .038804 | 313.89 |
| .00432 | .038448 | 316.79 |
| .00428 | .038092 | 319.76 |
| .00424 | .037736 | 322.77 |
| .00420 | .03738 | 325.85 |
| .00416 | .037024 | 328.98 |
| .00412 | .036668 | 332.18 |
| .00408 | .036312 | 335.43 |
| .00404 | .035956 | 338.75 |
| .00400 | .0356 | 342.14 |
| .00396 | .035244 | 345.59 |
| .00392 | .034888 | 349.12 |
| .00388 | .034532 | 352.78 |
| .00384 | .034176 | 356.39 |
| .00380 | .03382 | 360.15 |
| .00376 | .033464 | 363.98 |
| .00372 | .033108 | 367.89 |

For Gold, one calorie of heat:

Volume (cc): 0.0044 0.00436 0.00432 0.00428/00424 0.00420 0.00416 0.00412 0.00408 0.00404 0.00400 0.00396 0.00392 0.00388 0.00384 0.00380 0.00376 0.00372

Mass (g): 0.08448 0.083712 0.083944 0.082176 0.081408 0.08064 0.079872 0.079104 0.078336 0.077568 0.0768 0.076032 0.075264 0.074496 0.073728 0.07296 0.072192 0.071424

Temperature change (c): 374.59 378.03 381.53 385.09 388.72 392.43 396.20 400.05 403.97 407.97 412.05 416.21 420.46 424.79 429.22 433.73 438.35 443.07

For Silver, one calorie of heat:

Volume (cc): 0.004 0.00396 0.00392 0.00388 0.00384 0.00380 0.00376 0.00372

Mass (g): 0.04172 0.0413028 0.0408856 0.0404684 0.0400512 0.039034 0.0392168 0.0387996

Temperature change (c): 429.55 433.89 438.32 442.88 447.45 452.16 456.98 461.89

For titanium one calorie of heat:

| Volume (cc) | mass (g) |
|---|---|
| .0044 | .0198 |
| .00436 | .01962 |
| .00432 | .1944 |
| .00428 | .01926 |
| .00424 | .01908 |
| .00420 | .0189 |
| .00416 | .01872 |
| .00412 | .01854 |
| .00408 | .01836 |
| .00404 | .01818 |
| .00400 | .01800 |
| .00396 | .01782 |
| .00392 | .01764 |
| .00388 | .01746 |
| .00384 | .01724 |
| .00380 | .01710 |
| .00376 | .01692 |
| .00372 | .01674 |

Temperature change (c): 1836.54 1853.40 1870.56 1888.04 1905.85 1924.00 1 '942.50 1961.36 1980.59 2000.20 2020.30 2046.40 2061.43 2082.68 2104.38 2126.52 2149.15 2173.26

For Platinum, one calorie of heat:

| Volume (cc) | mass (g) |
|---|---|
| .0044 | .09402 |
| .00436 | .0951732 |
| .00432 | .0923184 |
| .00428 | .0914636 |
| .00424 | .0906088 |
| .00420 | .089754 |
| .00416 | .0888992 |
| .00412 | .0880444 |
| .00408 | .0871896 |
| .00404 | .0863348 |
| .00400 | .08548 |
| .00396 | .0846353 |
| .00392 | .0837704 |
| .00388 | .0829156 |
| .00384 | .06820608 |
| .003800 | .081206 |
| .00376 | .0803512 |
| .00372 | .0794964 |

Temperature change (c): 454.49 458.66 462.90 467.23 471.69 476.13 480.71 485.38 490.14 494.97 499.94 504.99 510 14 515.40 520.77 526.25 531.85 537.57

For Molybdenum, one cal heat:

| Volume (cc) | mass (g) |
|---|---|
| .00400 | .03604 |
| .00396 | .0356796 |
| .00392 | .0353192 |
| .00388 | .0349568 |
| .00384 | .0034598 |
| .00380 | .034238 |
| .00376 | .0338776 |
| .00372 | .0033156 |

Temperature change (c): 426.87 431.19 435.59 440.08 444.66 449.34 454.12 459.00

Using the teachings of the present invention, all of the elements that are in an ore body in elemental form may be separated. Solid inorganic compounds may be separated as well. Examples of such inorganic compounds are listed below:

| Name | formula | specific heat |
|---|---|---|
| Aluminum chloride | alcl4 | .188 |
| Aluminum fluoride | alf3 | .229 |
| Aluminum hydroxide | al(oh)4 | .177 |
| Aluminum oxide | al2O3 | .174 |
| Aluminum sulfate | al2(so4)3 | .184 |
| Iodide | nh4i | .111 |
| Nitrate | nh4no3 | .306 |
| Sulfate | (nh4)3s04 | .283 |
| Antimony trisulfide | sb2s3 | .0829 |
| Barium carbonate | baco3 | .0999 |
| Molybdate | camoo4 | .165 |
| Copper sulfate | cuso4h2o | .256 |
| Sulfide | cu2s | .129 |

One of ordinary skills in the art would recognize that the ore piece may be cooled down instead of being heated up, and then calculate the temperature change and use the specific heat to determine what the ore is, without departing from the scope of the present invention. The only important thing here is to add or withdraw a measurable quantity of heat to or from the ore.

The cooling down may be done by, for example, exposing the ore to a cool box or chamber, which may be mounted on the conveyor belt, for a controlled period of time. An alternative way of cooling the ore piece may be by dropping a known quantity of cold water, of known temperature, on the ore piece. The cooling of the ore piece may be a preferred alternative for changing the ore's temperature in certain environmental conditions, as for example, when the ore to be processed is already rather warm.

Variable Volume Alternative

The following are the steps that may be taken to process ore using this alternative method and system, characterized by the use of a variable/unknown volume of ore (or its components) in a cup and known amount of heat applied to the ore (or its components) as described below.

First, a single piece of ore is placed in a small cup. The temperature of the piece of ore is measured. This first measured temperature is sent to the computer. Known amount of heat is either added to the piece of ore or heat is extracted from the piece of ore.

Next, the temperature of the piece of ore is measured again. This second measured temperature is also sent to the computer. The computer then determines the temperature change, called delta T, by calculating the difference between the second and the first measured temperature.

Typically, the ore body has already had an assay done. Thus, the coefficient of heat for the minerals and waste in the ore are typically known from the assay.

The computer knows the amount of heat that was added to the cup with the small piece of ore or the amount of heat extracted from the cup with the small piece of ore. The computer also knows the temperature change calculated as described above, and it also knows the specific heat if a certain ore component (e.g., waste, cooper, etc) is assumed or expected to be in the cup. The computer uses then the equation, Heat (known)=specific heat (known)×mass×temperature change (known), to calculate the mass of the piece of ore in the cup.

Next, the temperature of the piece of ore is measured again. This third measured temperature is also sent to the computer.

The piece of ore is heated again or heat is extracted from the piece of ore, using also a known amount of heat. The amount of heat added or extracted this time may be the same or, for example, two to three times greater than the amount of heat used earlier, as described above. The computer can and will then calculate an expected temperature change, knowing the amount of heat applied this time, the mass of the piece of ore previously calculated as described above, and the same specific heat (e.g., specific heat of waste, if waste is expected).

Next, the temperature of the ore piece is measured again and this fourth measured temperature is also sent to the computer. The computer then determines if the piece or ore in the cup is waste by comparing the expected temperature change calculated as described above with the actual temperature change determined by computing the difference between the fourth and the third measured temperature. If the two temperature differences are equal, the piece of ore is pure waste and the cup will be dumped to the waste bin. If not, the cup will be dumped to the mineral bin, and the same process may be used to separate one-by-one the minerals from the mineral bin.

The variable volume method described above could also work with more than one piece of crushed ore placed in the cup. The above process would be the same. Furthermore, it should be apparent that the cup size may vary with the amount of ore placed in the cup.

Variable Heat Alternative

A variable heat ore processing alternative method and system, as described below, may be a good choice when, for example, the heating device is not very precise, when the amount of heat applied to the ore in an ore cup cannot be ascertained by the device, and/or when a less sophisticated heating device is used in order to make the process and the system less expensive.

What follows is a description of this alternative method and system.

In front of each cup is a metal disk 885 (FIG. 8) (or other shapes (e.g., rectangular shape 775, FIG. 7)) having a known volume and made from a known metal such as iron (Fe). Thus, the metal disk has its known specific heat. The disk is thermally insulated from the cups.

The temperature of the metal disk is measured (i.e., first disk temperature). Heat is added to or extracted from the disk using a heating or cooling device, for example, as described earlier herein. After the addition or extraction of heat, the temperature of the disk is measured again (i.e., second disk temperature). Both temperatures are sent to the computer. The computer calculates the temperature change (second temperature minus first temperature), and then, using the Heat=specific heat×mass×temperature change equation, it calculates the amount of heat that was added to (or extracted from) the metal disk.

Next, let's say that waste is being separated from the ore, and thus, the computer is expected to determine whether or not pure waste is present in the cups.

Because a precise/known volume of ore is in the cup, if it is assumed to be waste (for example) its mass is also known (volume×density). Also, the specific heat of the waste is known. Then, using the same formula: Heat (known)=specific heat (known)×mass (known)×temperature change, the computer calculates the expected temperature change, if using the same amount of heat used for the disc and calculated above, and if the ore in the cup is pure waste.

Next, the temperature (first ore/waste temperature) of the ore in the cup is measured and is sent to the computer. Next, the same amount of heat as applied to the metal disc is applied to the ore in the cup using the same or a duplicate heat device or source. This may be accomplished for example by exposing the ore to the same heat source for the same amount of time.

After applying the heat (adding or extracting), the temperature of the ore is measured again (second temperature) and the computer calculates the temperature change/difference between the two measured temperatures. If it is the same as the expected temperature change, the computer will determine that the ore in the cup is pure waste and it will dump it into the waste bin. If the two temperature changes (expected and measured) are not the same, the cup will be dumped into a mineral bin.

Similarly, minerals such as cooper may be separated from the ore.

Precise Volume and Precise Heat Alternative

The following are the steps that may be taken to process ore using this alternative approach characterized by the use of a known volume of ore (or its components) in a cup and known amount of heat applied to the ore (or its components) as described below. First, the ore body is assayed for a temperature range, preferably minus 20 degrees Celsius (c; centigrade) to 100 c. To do so, a cup is filled with a known volume of ore waste ("waste") and the temperature of the waste is brought, if not already there, to minus 20 c (i.e., initial or first temperature) by, for example, cooling it in a freezer. Waste may be any undesirable element/component of the ore to be processed such as granite. Next, a precise amount of heat is added to or extracted from the waste, employing for example methods and system described earlier, and the new temperature (i.e., final or second temperature) is measured and is sent to the computer.

Next, the process is repeated with the initial temperature of the waste in the cup of known volume being set preferably a tenth of a degree higher, to minus 19.9 c. Next, as before, a precise amount of heat is added to or extracted from the waste, employing for example methods and system described earlier, and the new temperature is measured and is sent to the computer. This process is repeated again and again for each tenth of degree increment, to 19.8, 19.7, and so on, to 100 degrees Celsius. Thus, at the end of this process, the computer has a look up table for the expected temperature of the waste when the waste receives (or loses) a precise amount of heat while the waste has a certain initial temperature that falls within the assayed range of minus 20 c to 100 c. It should be observed that, typically, the actual temperatures of the ore to be processed will fall within the minus 20 c to 100 c temperature range.

Next, the above assay process is also performed for each mineral (e.g., cooper, gold, etc) in the ore body.

Once all of the above assays are completed, and the data is stored into a computer, the ore may be processed. To do so, the cup is filled with a known volume of crushed ore and the initial/first temperature of the ore in the cup is measured and is sent to the computer. Next, the crushed ore of known volume in the cup has the same amount of heat, i.e., the amount of heat used in the assay described above, added to or extracted from it. Next, the second/final temperature is measured and is sent to the computer. The computer now knows what the cup contains (e.g., waste, cooper, etc) by using the look up tables recording the results of the assays previously performed as described above.

For example, if the first temperature measured is minus 19.5 and the second temperature measured is the same as the second temperature recorded by the computer during the assay of the waste having the initial temperature of minus 19.5 c, as described above, then the computer knows that the processed cup contains waste, and thus, will ensure that that the cup is dumped into the waste bin. Similarly, the computer will be able to dump each mineral in the exact mineral bin.

It should be noted that it may be preferred to separate one ore component at the time (e.g., waste first, cooper next, and so on). Thus, if for example, waste is to be separated from the ore first, the computer will be set to expect waste in the cups. Then, if the computer confirms that the ore in the cup is pure waste as described above, it will dump the cup into the waste bin; if not, it will dump it into a different (mineral) bin, the content of which will be next similarly processed to separate/extract the valuable minerals.

Regarding the assays described above, in order to save time and costs, once several assays were conducted for the entire temperature range of for example minus 20 c to 100 c, subsequently (e.g., at the time trucks are loaded with ore), the assays may be conducted for smaller temperature ranges (e.g., from minus 10 c to plus 20 c) and the obtained data may be used by the computer to extrapolate to a larger temperature range (e.g., minus 20 c to 100 c).

Preferably, the waste (and/or the other ore components) is constantly monitored for its specific heat. If the specific heat of the waste changes, the computer calculates a new look up table instantly and the operation continues.

Monitoring the Mineral to Waste Ratio

There may be a need to constantly monitor the mineral(s) to waste, mineral(s) to ore, and/re waste to ore ratio during the processing of the ore using any of the above described ore processing methods and systems. Knowing such ratio may, for example, help determine whether or not the processing of the ore makes economic sense. For example, if it was determined that any ore with a mineral content less than 1% is not worth processing, monitoring the ore during processing may help determine if the ore brought to the processing plant by the trucks during a certain time period, and/or from a certain site, falls below the required 1%. If it does, the processing of the ore may need to be stopped and the ore may need to be dumped to the waste pit. Then, a new, richer ore will be need from another site to process.

For the mineral ratio monitoring to be used, an assay of the ore body is typically done first, and the assay data is stored in the computer to create a look up table for use by the computer during the actual processing of the ore.

For simplification purposes, let's assume that the ore contains waste and only one valuable mineral. To conduct the assay, typically, a precise volume of 100% waste is placed in a cup, a first temperature of the waste is measured, a precise amount of heat is added to or extracted from the waste, a second temperature of the waste is measured, and then the computer calculates the temperature change, delta T for waste. It should be noted that, alternatively, the computer may use the Heat=specific heat×mass×temperature change equation to compute the temperature change, delta T, when the cup's content is 100% waste if the specific heat and the density of the waste are known. Thus, no actual assay is needed if the computer is asked to compute the temperature change using the above equation.

Next, the assay is continued or the computer is asked to use the above equation to determine the temperature change when the waste ratio in the cup increases or decreases by 0.01 percent, as follows:

| Waste volume (%) | Mineral volume (%) | Temperature change |
| --- | --- | --- |
| 99.99 waste | .01 mineral | delta T1 |
| 99.98 waste | .02 mineral | delta T2 |
| 99.97 waste | .03 mineral | delta T3, | and so on, to:

| | | |
| --- | --- | --- |
| .01 waste | 99.9 mineral | delta T999 |
| Zero waste | 100 mineral | delta T1000 |

All the data obtained above is stored in the computer as a look up table. Now, during the ore processing, the cup is, for example, filled with a precise/known volume of crushed ore, a first temperature T1 is measured and sent to the computer; a precise amount of heat is then added to or extracted from the ore; after the heat is added or extracted, a second temperature T2 is measured and sent to the computer, which calculates the temperature change by subtracting T1 from T2. The computer now uses the look up table obtained as described above and determines if the cup is 100% waste. If the cup isn't 100% waste, the computer determines the ratio of mineral (e.g., 1.2% by volume) by using the look up table to identify the matching temperature change, stores this information, and dumps the cup in the mineral bin.

Again, if the mineral ratio average for a certain period of time is greater than the minimum acceptable (e.g., 1%), processing continues. If not, again, processing may be stopped and ore from another source (e.g., richer blast site) may be needed.

It should also be noted that, at the end of the day the mineral ratio in the mineral bin is also known. The computer may easily calculate an average mineral ratio (e.g., 1.24%) of all cups that were processed and dumped into the mineral bin.

Although specific embodiments have been illustrated and described herein for the purpose of disclosing the preferred embodiments, someone of ordinary skills in the art will easily detect alternate embodiments and/or equivalent variations, which may be capable of achieving the same results, and which may be substituted for the specific embodiments illustrated and described herein without departing from the scope of the present invention. Therefore, the scope of this application is intended to cover alternate embodiments and/or equivalent variations of the specific embodiments illustrated and/or described herein. Hence, the scope of the present invention is defined only by the accompanying claims and their equivalent.

What is claimed is:

1. A method of ore processing comprising in any order the steps of:
   assaying the ore to determine what ore constituent has to be separated;
   heating or cooling a metal object using controlled means for adding or extracting heat, for the purpose of determining the amount of heat added or extracted by said controlled means for adding or extracting heat;
   determining the expected temperature change of the ore constituent that has to be separated if the same amount of heat is added to or extracted from it;
   measuring a first temperature of a substantially precise volume of the ore;
   changing the first temperature of the substantially precise volume of the ore, immediately after the measuring of the first temperature, by exposing the substantially precise volume of the ore to the same controlled means for adding or extracting heat, such that the same amount of heat is added to or extracted from the substantially precise volume of the ore;
   measuring a second temperature of the substantially precise volume of the ore immediately after the controlled means for adding or extracting heat have been disengaged and determining the resulting measured temperature change of the substantially precise volume of ore; and,
   determining that the substantially precise volume of the ore in the cup consists substantially of the ore constituent that has to be separated if the measured temperature change is the same as the expected temperature change.

2. The method of claim 1, wherein said metal object is a metal disk.

3. The method of claim 2, further comprising placing a metal disk near each of a plurality of cups; loading a substantially precise volume of the ore in each of the plurality of cups; for each of the plurality of cups, measuring a first disk temperature of the nearby disk, changing the first disk temperature, immediately after the measuring of the first disk temperature, by exposing the nearby disk to the controlled means for adding or extracting heat, measuring a second disk temperature of the nearby disk immediately after the controlled means for adding or extracting heat have been disengaged; and, determining the amount of heat added or extracted from the nearby disk.

4. The method of claim 1, further comprising monitoring the ratio of the ore constituent that has to be separated by comparing the measured temperature change with temperature changes from a look up table.

5. The method of claim 1, wherein the controlled means for adding or extracting heat comprise at least one member of a group consisting of a laser, a current supply and a cooling chamber.

6. The method of claim 1, wherein the temperature measurements are performed by at least one member of a group consisting of a digital optical thermometer and a digital contact thermometer.

7. The method of claim 1, wherein the controlled means for adding or extracting heat include at least a metal arm and at least a metal guide assembly wherein the at least a metal arm is attached to each of the plurality of cups.

8. The method of claim 3, wherein each of the plurality of cups comprises a unique identifier.

* * * * *